(12) United States Patent
Kim

(10) Patent No.: US 11,511,107 B2
(45) Date of Patent: Nov. 29, 2022

(54) BEAUTY CARE DEVICE USING PLASMA

(71) Applicant: AIRBIO Inc., Seoul (KR)

(72) Inventor: Min Ki Kim, Seoul (KR)

(73) Assignee: AIRBIO Inc.

( * ) Notice: Subject to any disclaimer, the term of this patent is extended or adjusted under 35 U.S.C. 154(b) by 1069 days.

(21) Appl. No.: 16/047,281

(22) Filed: Jul. 27, 2018

(65) Prior Publication Data

US 2019/0070407 A1 Mar. 7, 2019

Related U.S. Application Data

(63) Continuation of application No. PCT/KR2017/000703, filed on Jan. 20, 2017.

(30) Foreign Application Priority Data

Jan. 29, 2016 (KR) ........................ 10-2016-0011225

(51) Int. Cl.
*A61B 18/04* (2006.01)
*A61N 1/04* (2006.01)
(Continued)

(52) U.S. Cl.
CPC .......... *A61N 1/0472* (2013.01); *A61B 18/042* (2013.01); *A61N 1/04* (2013.01);
(Continued)

(58) Field of Classification Search
CPC .......... A61N 1/0472; A61N 1/04; A61N 1/18; A61N 1/328; A61N 1/44; A61B 18/042; A61B 2018/00452
See application file for complete search history.

(56) References Cited

U.S. PATENT DOCUMENTS

2011/0237921 A1* 9/2011 Askin, III ................ A61B 5/24
607/116
2013/0345620 A1* 12/2013 Zemel .................. A61B 18/042
604/24
(Continued)

FOREIGN PATENT DOCUMENTS

KR 10-2013-0023588 A 3/2013
KR 10-1407672 B1 6/2014
(Continued)

OTHER PUBLICATIONS

Korean Office Action (KR 10-2016-0011225), KIPO, dated Mar. 30, 2016.
(Continued)

*Primary Examiner* — Ankit D Tejani
*Assistant Examiner* — Joshua Brendon Solomon
(74) *Attorney, Agent, or Firm* — Park & Associates IP Law, P.C.

(57) ABSTRACT

Skin treatment device by application of plasma to a skin, the device includes: a body having a handle; and an electrode unit generating an atmospheric pressure plasma by application of electric power, wherein first and second grounds are provided on two opposite sides of the handle, respectively, wherein the electrode unit is detachably attached to a mounting portion recessed from one surface of the body, wherein the electrode unit comprises: a first film, a second film, and a third film laminated together; and a first conductor disposed between the first and second films, and a second conductor disposed between the second and third films, such that a dielectric barrier discharge is generated between the first and the second conductors.

7 Claims, 8 Drawing Sheets

(51) Int. Cl.
    *A61N 1/18*     (2006.01)
    *A61N 1/44*     (2006.01)
    *A61N 1/32*     (2006.01)
    *A61B 18/00*     (2006.01)

(52) U.S. Cl.
    CPC ............... *A61N 1/18* (2013.01); *A61N 1/328* (2013.01); *A61N 1/44* (2013.01); *A61B 2018/00452* (2013.01)

(56) References Cited

U.S. PATENT DOCUMENTS

2017/0216614 A1*   8/2017   Weltmann ............ A61B 18/042
2018/0169427 A1*   6/2018   Jeon ......................... A61N 1/44

FOREIGN PATENT DOCUMENTS

| KR | 10-1568380 B1 | 11/2015 |
| KR | 10-1577207 B1 | 12/2015 |
| KR | 10-1635718 B1 | 7/2016 |

OTHER PUBLICATIONS

Korean Decision to Grant (KR 10-2016-0011225), KIPO, dated Apr. 29, 2016.
International Search Report (PCT/KR2017/000703), WIPO, dated Jun. 2, 2017.

\* cited by examiner

BEAUTY CARE DEVICE USING PLASMA

REFERENCE TO RELATED APPLICATIONS

This is a continuation of International Patent Application PCT/KR2017/000703 filed on Jan. 20, 2017, which designates the United States and claims priority of Korean Patent Application No. 10-2016-0011225 filed on Jan. 29, 2016, the entire contents of which are incorporated herein by reference.

FIELD OF THE INVENTION

The present invention relates to an apparatus for generating plasma for beauty care or skin treatment.

BACKGROUND OF THE INVENTION

Plasma is a gas state in which electrons with negative charge and positively charged ions are separated at significantly high temperature. At this time, the charge separation is considerably high, but the number of positive and negative charges is the same overall, and thus, resulting in neutral electric charge as whole.

In general, the state of a substance is divided into three states, namely, solid, liquid, and gas states. Plasma is often referred to as the fourth states of matter. When energy is applied to a solid, it becomes a liquid, and then, a gas. When high energy is applied to the gas substance, the gas is separated into electrons and atomic nuclei at tens of thousands of degrees Celsius, thereby becoming a plasma state.

To create a plasma state, it is often necessary to apply an electrical method such as direct current, microwave, or electron beam to generate plasma, and then use a magnetic field to maintain this state.

Plasma has many classification criteria such as plasma density, electron temperature, degree of thermal equilibrium between species, generation methods, and application fields, but it is most basic to classify it into plasma density and electron temperature. The plasma can be divided into local thermal equilibrium (LTE) and non-local thermal equilibrium (non-LTE) by the degree of thermal equilibrium. The term "local thermal equilibrium" means that the temperatures of all of the plasma particles are in the same thermodynamic state in the localized region of the plasma.

Plasma used for research and manufacturing processes is usually one of LTE or non-LTE, and the former is commonly referred to as thermal plasma and the latter as low-temperature or cold plasma.

The present invention is directed to a method for providing a beauty care device for generating a low-temperature plasma, in particular, an atmospheric pressure plasma among the low-temperature plasma.

Atmospheric pressure plasma is mainly used for surface modification, coating, and environmental purification of materials. Recently, researches have been extended to applications in biomedical applications and biomedical applications as well.

Accordingly, the present invention is directed to a beauty care device which is harmless to the human body while using atmospheric plasma, and which can be portable.

SUMMARY OF THE INVENTION

It is an object of the present invention to provide a beauty care or skin treatment device using plasma, with a more improved structure and having a complex function.

In order to solve the problems of the conventional art, the present invention provides, according to one aspect thereof, a plasma beauty/skin care apparatus which comprises: a body having a handle; and an electrode unit generating an atmospheric pressure plasma by application of electric power, wherein first and second grounds are provided on two opposite sides of the handle, respectively, the electrode unit is detachably attached to a mounting portion recessed from one surface of the body, the electrode unit comprises: a first film, a second film, and a third film laminated together; and a first conductor disposed between the first and second films, and a second conductor disposed between the second and third films, such that a dielectric barrier discharge is generated between the first and the second conductors.

In order to solve the problems of the conventional art, the present invention provides, according to another aspect thereof, a plasma beauty/skin care apparatus which comprises: a body having a handle; and an electrode unit generating an atmospheric pressure plasma by application of electric power, wherein first and second grounds are provided on two opposite sides of the handle, respectively, the electrode unit is detachably attached to a mounting portion recessed from one surface of the body, the electrode unit comprises: a first film and a second film laminated together; a first conductor and a second conductor disposed between the first and second films, the first conductor and the second conductor are spaced apart from each other.

In order to solve the problems of the conventional art, the present invention provides, according to another aspect thereof, a plasma beauty/skin care apparatus which comprises: a body having a handle; and an electrode unit generating an atmospheric pressure plasma by application of electric power, wherein first and second grounds are provided on two opposite sides of the handle, respectively, the electrode unit is detachably attached to a mounting portion recessed from one surface of the body, the electrode unit comprises: a first dielectric member having a plate shape, a second dielectric member laminated on the first dielectric member, and a conductive electrode disposed between the first and second dielectric members, such that a dielectric barrier discharge is generated between the first and second dielectric members and the conductive electrode.

In order to solve the problems of the conventional art, the present invention provides, according to another aspect thereof, a plasma beauty/skin care apparatus which comprises: a body having a handle; and an electrode unit generating an atmospheric pressure plasma by application of electric power, wherein first and second grounds are provided on two opposite sides of the handle, respectively, the electrode unit is detachably attached to a mounting portion recessed from one surface of the body, the electrode unit comprises: a first conductive unit in the form of a wire; a second conductive unit surrounding the first conductive unit and twisted to form a plurality of turns; and an insulating sheath formed on at least one of the first and second conductive units so as to generate a dielectric barrier discharge.

According to another embodiment of the present invention, the body further comprising an AC generator supplying power to the conductors, a frequency of the alternating voltage is several kHz to several hundred kHz, the AC generator operated in a pulse mode having a pulse frequency of several Hz to several hundred Hz.

According to another embodiment of the present invention, one of the conductors is electrically connected to one of the grounds.

According to another embodiment of the present invention, the body further comprises an elastic body provided between the mounting portions of the electrode unit, the elastic body is configured to emit radicals to the surroundings at the time of discharge by vibrating the electrode unit.

According to another embodiment of the present invention, the electrode unit is configured to have a wide band shape elongated in the longitudinal direction to generate plasma at a larger area, both sides of the electrode unit are detachably coupled to the body According to another embodiment of the present invention, the first conductor and the second conductor are spaced apart from each other so as not to be laminated when projected on one surface thereof, at least one of the first and second conductors include at least three or more conductive lines that are divided in branches.

According to the present invention having the above-described structures, the skin care or treatment apparatus using the plasmas has an effect of improving the density of the skin or dermis by an antioxidant action, thereby improving wrinkles and skin elasticity. It also improves the tone of the skin and increases the permeability of the skin remedy agent into the dermis and skin. Also, by using the beauty care device, the sterilizing effect can be improved and the cleanness of the skin can be maintained.

DETAILED DESCRIPTION OF THE INVENTION

Figure 1:
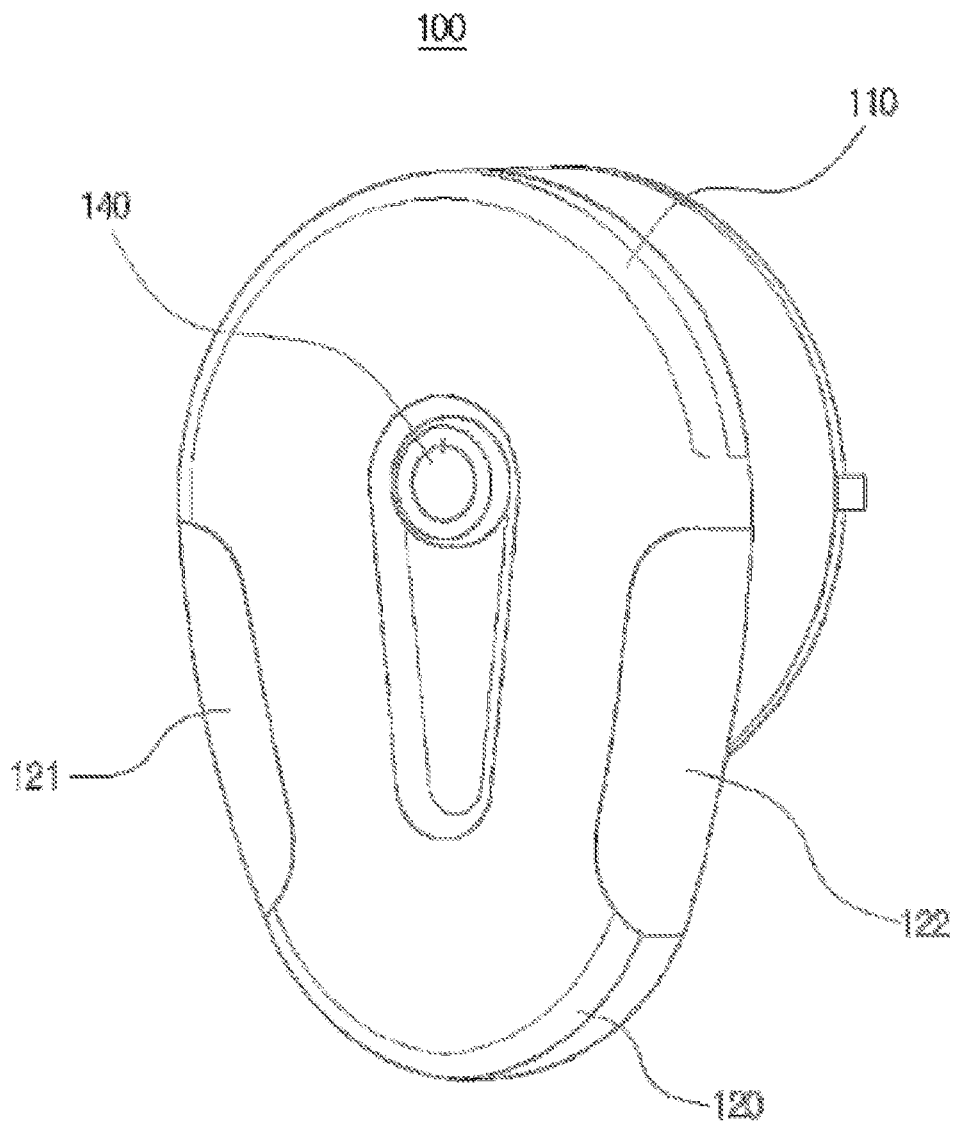
FIG. 1 is the front perspective view of the personal care appliance using plasma related to the embodiment of this invention.

Hereinafter, a beauty care apparatus using plasma according to the present invention will be described in detail with reference to the drawings. The suffix terms "module" and "part" used for constituent elements in the following description are given or used in consideration of ease of description, and do not have separate meanings or roles of their own. In this specification, the same or similar reference numerals are given to different embodiments in the same or similar configurations, and the description thereof is provided with the first description thereof. As used herein, the singular forms "a", "an" and "the" include plural referents unless the context clearly dictates otherwise.

Figure 2:
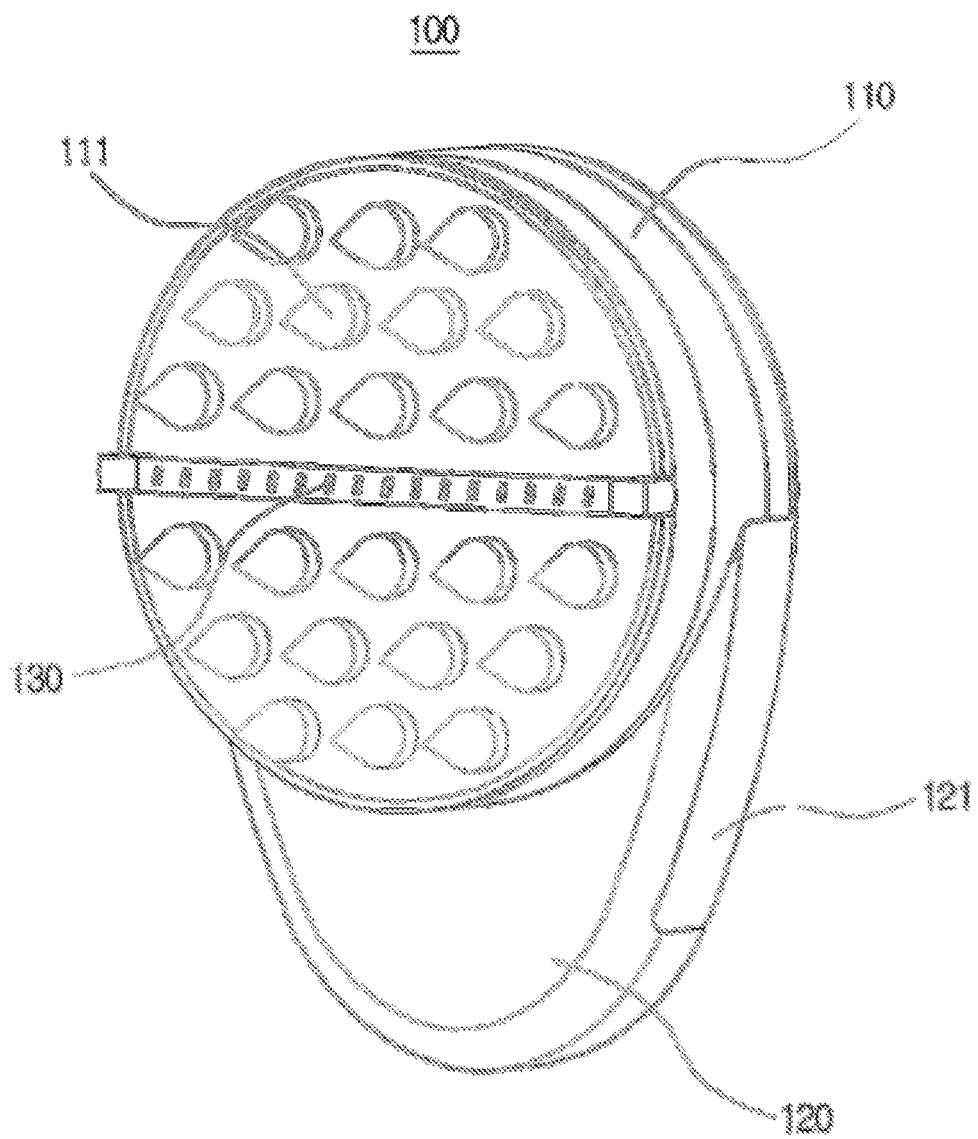
FIG. 2 is the back perspective view of the personal care appliance using plasma related to the embodiment of this invention.
Figure 3:
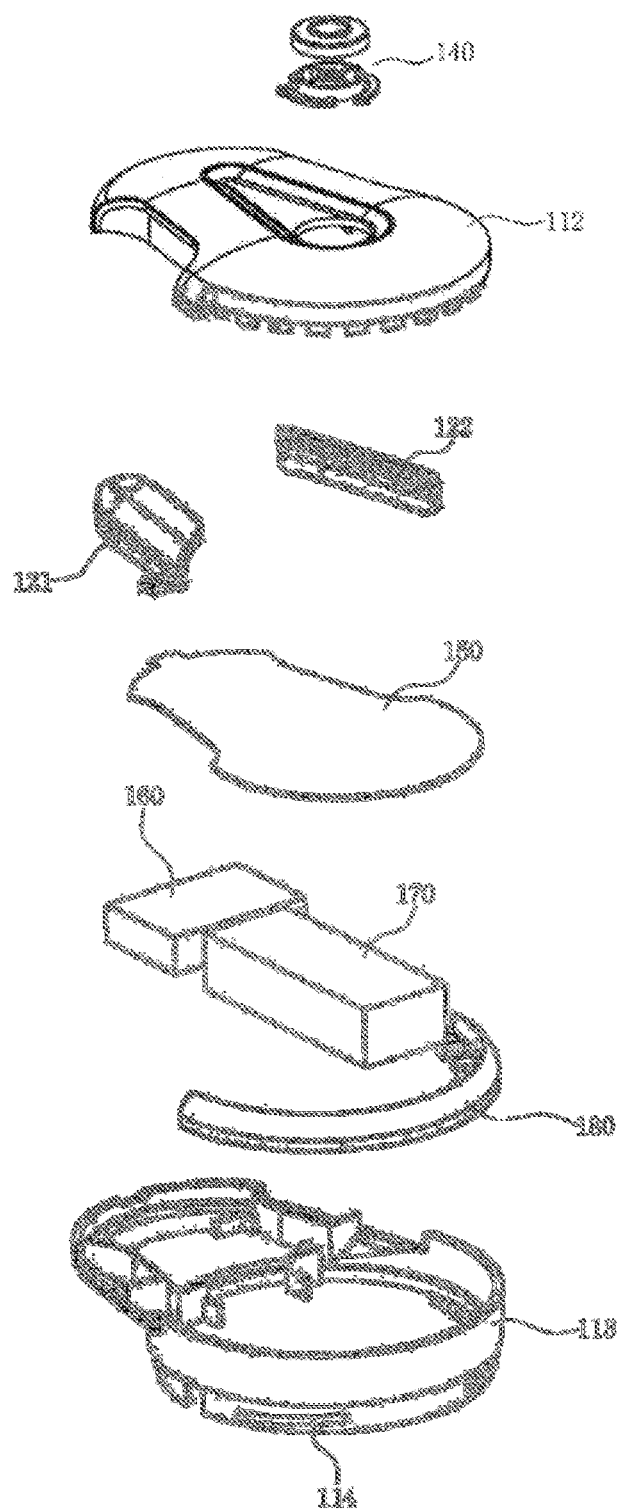
FIG. 3 is the disassembled perspective view of the personal care appliance using plasma of FIG. 1.
Figure 4:
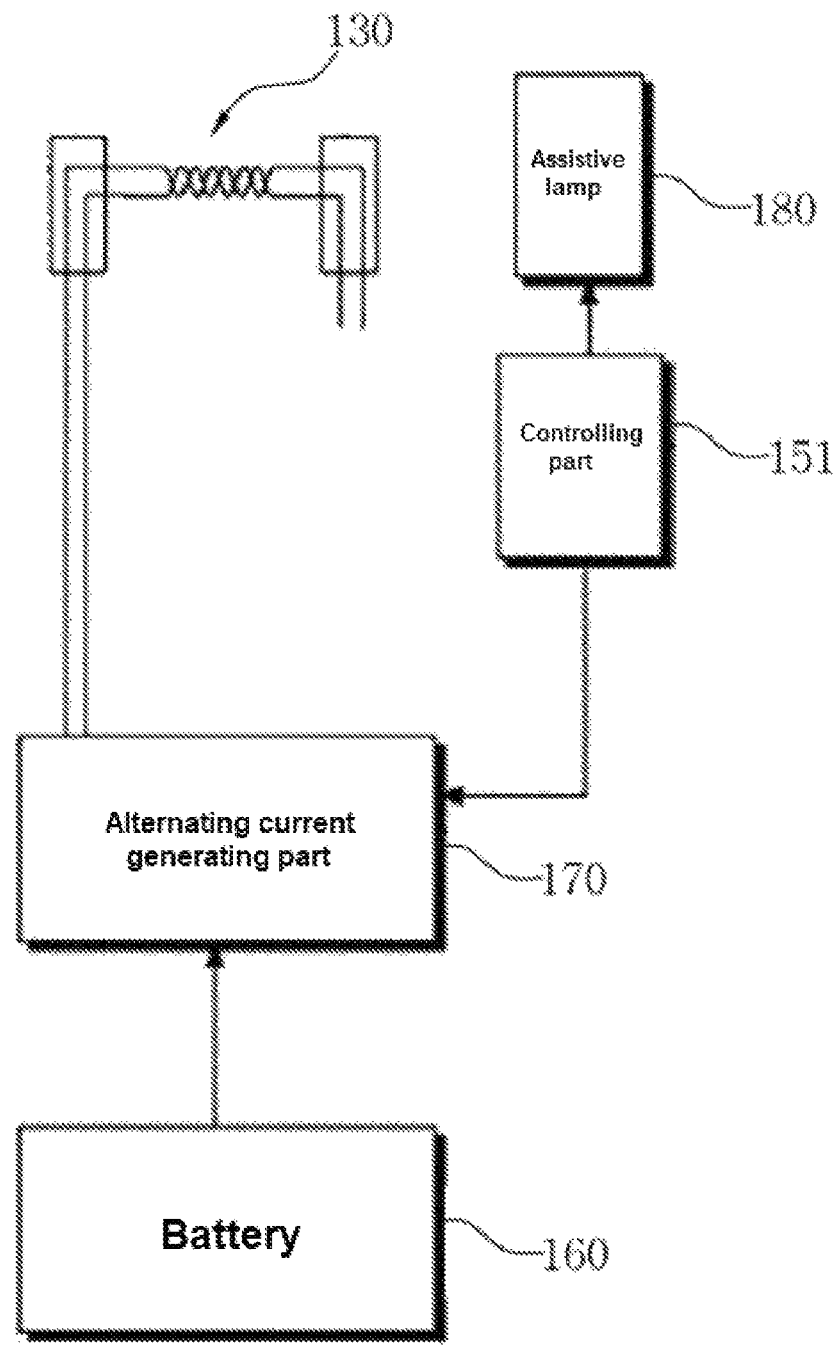
FIG. 4 is the schematic Figure of the personal care appliance using plasma of FIG. 1.

FIG. 1 is the front perspective view of the personal care appliance using plasma related to the embodiment of this invention; FIG. 2 is the back perspective view of the personal care appliance using plasma related to the embodiment of this invention; FIG. 3 is the disassembled perspective view of the personal care appliance using plasma; FIG. 4 is the schematic Figure of the personal care appliance using plasma of FIG. 1.

Referring to FIG. 1 to FIG. 4, the beauty care device 100 includes body 110, 120 and electrode 130.

Referring to FIG. 1, bodies 110 and 120 constitute the outer appearance of the device 100, and are formed in a bar or similar shape so that the user can grip the device easily. Operation unit 140 is provided on the upper surfaces of the bodies 110 and 120, and grounds 121 and 122 are provided on both sides of the bodies 110 and 120. The operation unit 140 on the upper surface is used to receive a command for controlling the operation of the beauty care apparatus 100, and may include a plurality of input keys. The input keys can be employed in any manner as long as the user can operate in a tactile or similar manner. For example, a dome switch or touch screen capable of receiving a command or information by a push or touch operation of a user, a touch pad, a wheel for rotating a key, a jog method, or a joystick can be used.

The grounds are provided on both sides of the bodies 110 and 120, respectively. A first ground 121 is formed on one side of the bodies 110 and 120 and a second ground 122 on the other side of the bodies 110 and 120. Each of the grounds 121 and 122 may be electrically connected to the electrode unit 130 via a circuit board 150 or may be directly connected to the electrode unit 130.

Referring to FIG. 2, the electrode unit 130 is exposed on the rear surface of the body 110, 120. In addition, a spacing portion may be formed along the electrode unit 130 to leave a suitable space between the electrode unit 130 and the skin. The body 110 and 120 can be divided into an upper/left portion 110 and a lower/right portion 120, and the electrode unit 130 and the operation unit 140 are formed on the upper portion 110 and the lower portion 120, respectively. The lower portion 120 corresponds to a grip portion formed to be gripped by a user, and the grounds 121 and 122 may be formed on the grip portion.

Figure 5:
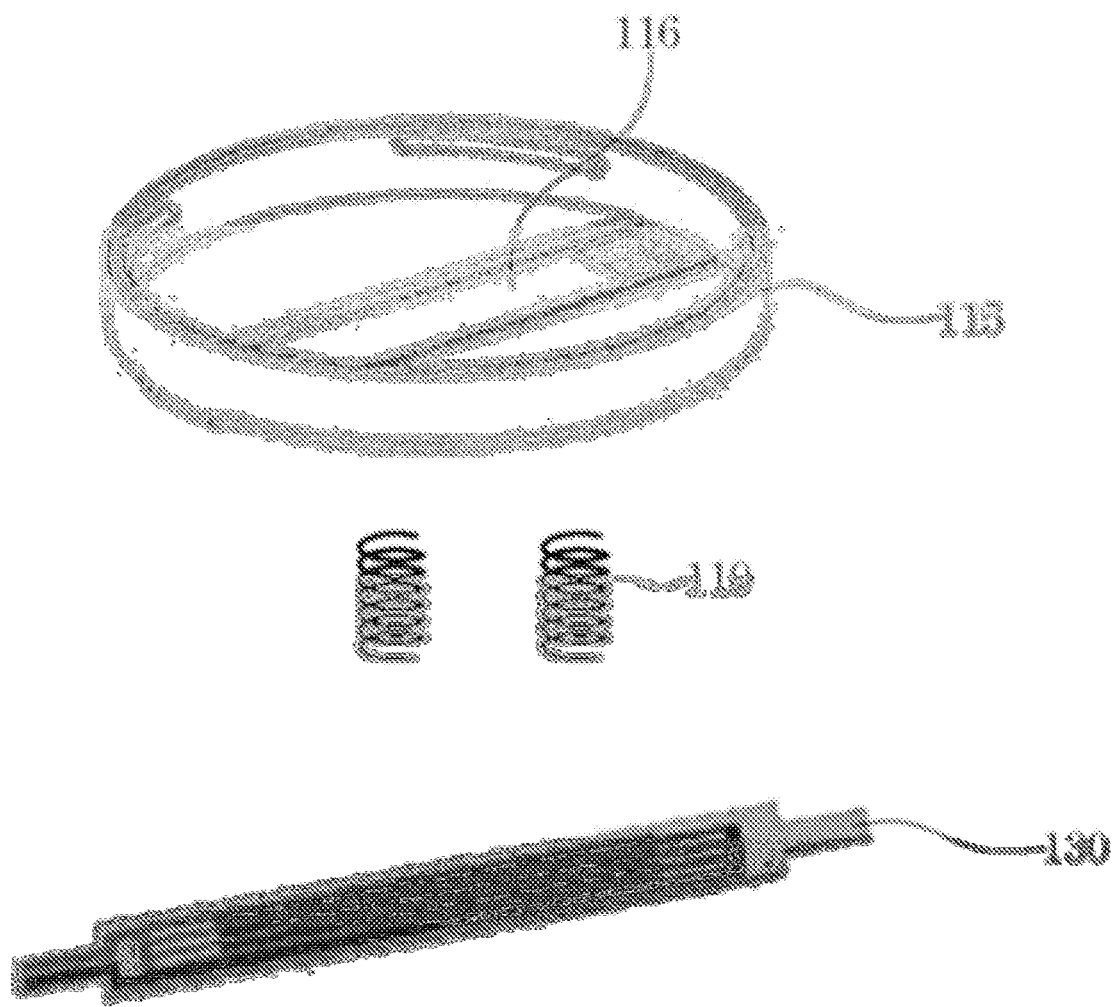
FIG. 5 is the drawing of the connecting part and the electrode part according to Embodiment 1.
Figure 6:
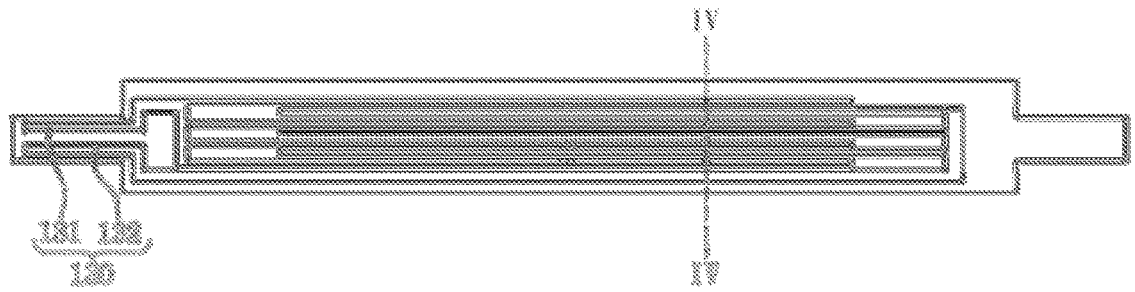
FIG. 6 is plan of the electrode part according to Embodiment 1.
Figure 8:
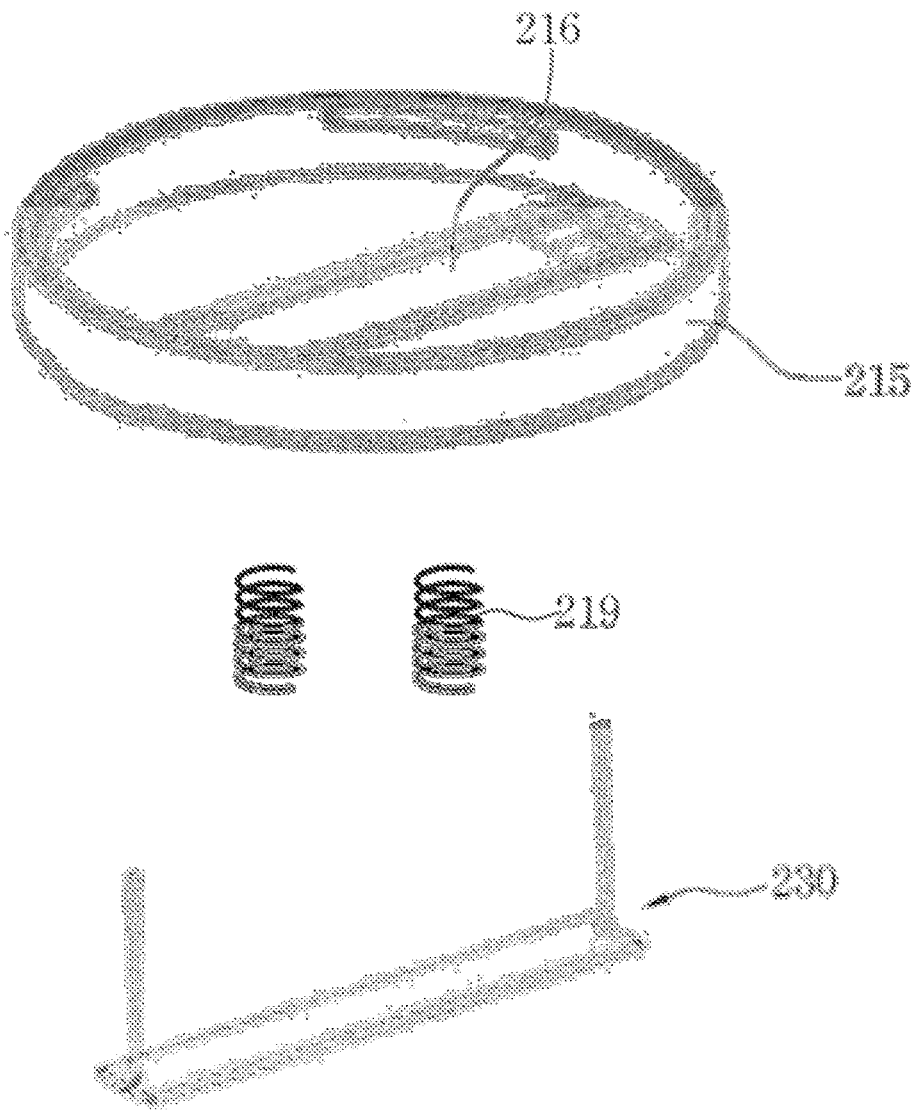
FIG. 8 is the drawing of the connecting part and the electrode part according to Embodiment 2.
Figure 10:
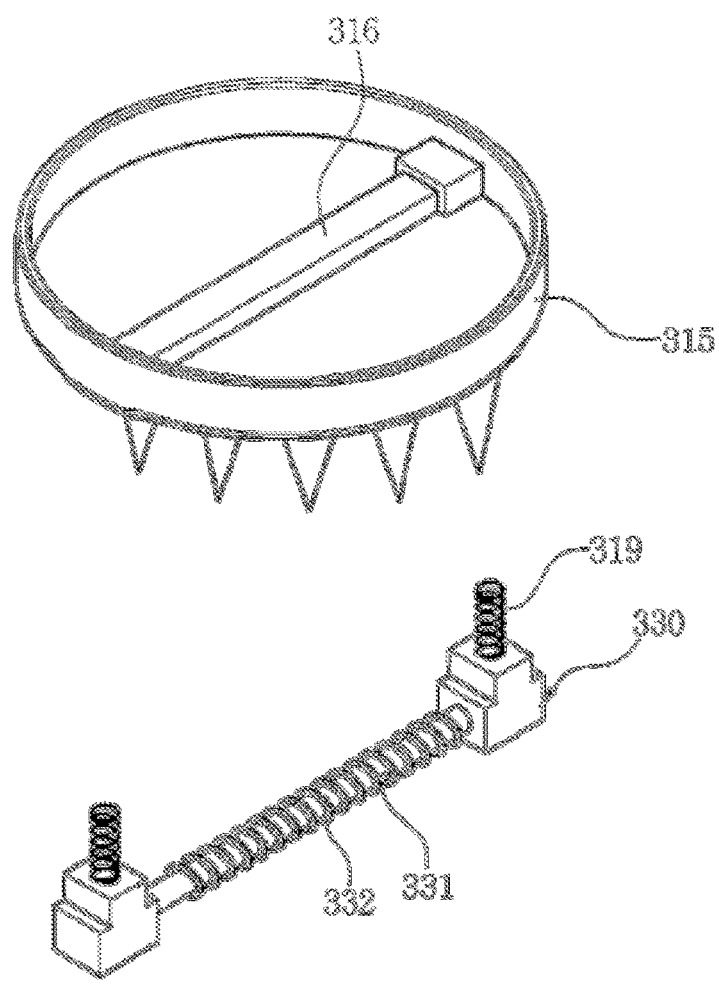
FIG. 10 is the drawing of the connecting part and the electrode part according to Embodiment 3.

Referring to FIG. 3, the case constituting the external appearance of the bodies 110 and 120 may include a front case 112, a rear case 113, and electrode cases 115, 215, and 315 (115, 215, 315 as shown in FIGS. 5, 8, 10 for reference).

Various parts are embedded in the space formed between the front case 112 and the rear case 113. The cases may be formed by injection molding with a synthetic resin or may include a metal material such as stainless steel (STS) or titanium (Ti).

Referring to FIG. 3 and FIG. 4, a battery 160, an AC generator 170, a controller 151, and an auxiliary lamp 180 are received in the space between the front case 112 and the rear case 113.

Battery 160 may be a rechargeable battery such as a lithium-polymer battery. The battery 160 is disposed in a space formed between the front case 112 and the rear case 113, and is capable of supplying DC power to the AC generating member 170.

The AC generator 170 can change the DC voltage to a high-voltage AC voltage. The AC generator 170 may include an inverter. The frequency of the alternating voltage may be from a few kHz to a few hundred kHz. The peak-to-peak ac voltage may be between 3 kV and 8 kV. The output waveform of the AC generator 170 may be a sinusoidal waveform. The AC generator 170 can output a high-voltage AC pulse at a pulse frequency of several Hz to several kHz. Specifically, the driving frequency of the AC generator 170 may range from several kHz to tens of kHz. The alternating current generating member 170 can operate in a pulse mode at a pulse frequency of several Hz to several hundred Hz. A stable dielectric barrier discharge can be performed at the pulse frequency and the driving frequency.

The control unit 151 controls the overall operation of the device 100. For example, the control unit 151 may control the duty ratio of pulses of the AC generator 170 and the output of the AC generator 170. Also, the control unit 151 operates by input of the operation unit 140 and can display the operation state of the device 100 on a display unit (not shown). The control unit 151 can also control the auxiliary lamp 180. The control unit 151 can be implemented using at least one of processors, controllers, micro-controllers, and microprocessors mounted on the circuit board 150, and other electronic units for performing and controlling various functions of the device.

The auxiliary lamp 180 may be disposed between the front case 112 and the rear case 113, or may be placed while being exposed to an external area of the front or rear cases 112, 113. The on/off operation of the auxiliary lamp 180 is controlled by the controller 151, and it may be in the form of an ultraviolet LED or an infrared LED. The auxiliary lamp 180 may be turned on in synchronization with the plasma generation of the device.

The battery 160 may be embedded in the bodies 110 and 120 or may be detachably attached to the bodies 110 and 120. It may be rechargeable lithium-polymer battery. The battery 160 may be disposed in a storage space of the housing. For replacement of the battery 160, the housing body parts and the coupling part may be designed to be disassembled and recoupled with each other. The battery 160 may supply DC power to the AC generator 170.

The AC generator 170 can change the DC voltage to a high-voltage AC voltage. The AC generator 170 may include an inverter. The frequency of the alternating voltage may be several kHz to several hundred kHz. The peak-to-peak ac voltage may be between 3 kV and 8 kV. The output waveform of the AC generator 170 may be a sinusoidal waveform. The AC generator 170 can output a high-voltage AC pulse at a pulse frequency of several Hz to several kHz. Specifically, the driving frequency of the AC generator 170 may range from several kHz to tens of kHz. The alternating current generating member 170 can operate in a pulse mode at a pulse frequency of several Hz to several hundreds Hz. A stable dielectric barrier discharge can be performed at this pulse frequency and driving frequency.

The power source to be applied to the electrode unit can control the discharge on-off time of the plasma by using PWM type pulses. The generation amount of ions can be controlled according to the control of the on and off times of the plasma, and the surface temperature can also be controlled according to the plasma discharge control, and as a result, the damage of the electrode unit and the skin can effectively be avoided. However, if the conventional CW (Continue Wave) pulses are used, the surface temperature cannot be controlled effectively, and the plasma can damage and burn the skin during the operation. In addition, the oxidation of the electrode can be accelerated, and this may cause an arc discharge due to damage of the electrode surface, reducing the life of the plasma device.

The controller 151 controls the duty ratio of pulses of the AC generator 170 and controls the output of the AC generator 170. In addition, the control unit 151 may be operated by a switch, and may display the operation state on the display unit 123.

Figure 7:
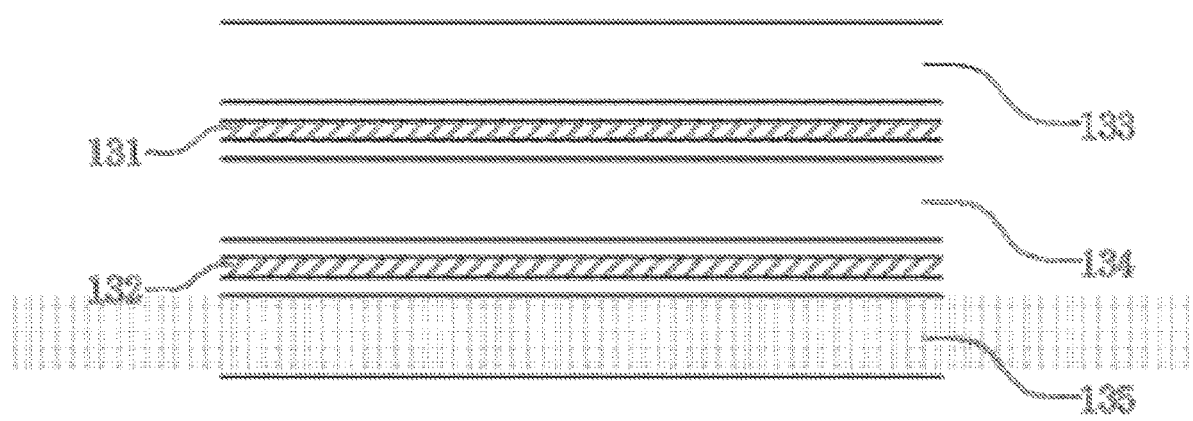
FIG. 7 is the sectional view of FIG. 5 cut along the line IV-IV.

FIG. 5 is a drawing of the electrode case 115 and the electrode part 130 according to Embodiment 1, and FIG. 7 is the sectional view of FIG. 5 cut along the line IV-IV.

The electrode case 115 is detachably coupled to the rear case 113. For this, a guide protrusion is formed on the inner circumference of the electrode case 115, and a guide may be formed on the outer circumference of the rear case 113. Thus, the electrode case 115 is screwed or fitted to the rear case 113.

The electrode unit 130 according to the second embodiment is formed in a thin plate shape. The electrode unit 130 is detachably mounted to the recessed portion 116 from one surface of the electrode case 115. The electrode unit 130 forms atmospheric plasma by the applied electric power. The electrode unit 130 may include a first conductor 131 and a second conductor 132 to generate a dielectric barrier discharge for atmospheric plasma. The electrode unit 130 is formed by stacking at least three films, and a first conductor 131 is formed between the first film 133 and the second film 134, and a second conductor 132 is formed between the second film 134 and the third film 135. The film may be a polyimide film. The electrode unit 130 may be formed of FPCB (FLEXIBLE PRINTED CIRCUIT BOARD).

The electrode unit 130 can have a wide band shape elongated in the longitudinal direction to generate plasma at a larger area. The first conductor 131 and the second conductor 132 are spaced apart from each other so as not to be laminated when projected on one surface. Also, at least one of the first conductor 131 and the second conductor 132 has at least three conductive lines that are divided in branches. With this configuration, a dielectric barrier discharge occurs between the conductive lines facing each other. As a result, plasma can be efficiently generated in a wider area.

The first conductor 131 and the second conductor 132 is made of a conductive material, for example, such as copper. The positive power of the alternating current generator 170 can be applied to the first conductor 131, and the negative power of the alternating current generator 170 can be applied to the second conductor 132. Also, a high-voltage alternating current pulse may be applied between the first conductor 131 and the second conductor 132. Accordingly, a dielectric barrier discharge can be generated between the first conductor 131 and the second conductor 132. The plasma generation region can be formed at a location where the discharge gap is maintained at an optimum distance between the first conductor 131 and the second conductor 132.

The first conductor 131 and the second conductor 132 may be exposed at one side of the electrode unit 130 and connected to the circuit board 150. One of the conductors can be connected to the first or second ground formed on the bodies 110 and 120 and the other can be connected to the alternating current generator 170.

The electrode case 115 is provided with a mounting portion 116 recessed from one side thereof. An elastic body 119 is mounted between the mounting portions 116 and the electrode unit 130. Therefore, the electrode unit 130 vibrates during discharging, and radicals can be emitted to the surroundings. The elastic body 119 may be, for example, a coil-shaped spring, but may be a plate-shaped spring. Also, the electrode unit 130 itself may be made of a member having elasticity.

In a modification of the electrode unit according to the second embodiment, the electrode unit may include a first film, a second film, and a first conductor and a second conductor provided between the first film and the second film. The first conductor and the second conductor are spaced from each other on the same plane, and the spacing between the conductors can be from a few micrometers to a few millimeters. With this configuration, the amount of generated atmospheric plasma ions can be controlled according to the interval.

Figure 9:
FIG. 9 is the sectional view of the electrode part according to Embodiment 2.

FIG. 8 is a drawing of the electrode case 215 and electrode unit 230 according to Embodiment 2, and FIG. 9 is the sectional view of the electrode unit 230 according to Embodiment 2.

The electrode case 215 is detachably coupled to the rear case 113. For this, a guide protrusion is formed on the inner circumference of the electrode case 215, and a guide may be formed on the outer circumference of the rear case 113. Thus, the electrode case 215 is screwed or fitted to the rear case 113.

The electrode unit 230 according to the first embodiment has a plate shape in which a plurality of dielectric members overlap with each other. The electrode unit 230 is detachably mounted on the recessed portion 216 from one surface of the electrode case 215. The electrode unit 230 forms atmospheric plasma by the applied electric power. The electrode unit 230 may include a first dielectric member 231, a second dielectric member 232, and a conductive electrode 233 to generate a dielectric barrier discharge for the atmospheric plasma. Any one of the dielectric members may be exposed towards the skin. The conductive electrode 233 may be affixed on one surface of the dielectric member.

The thickness of the first dielectric member 231 may range from a few hundred micrometers to several millimeters. The first dielectric member 231 may have a sufficient thickness to suppress an abnormal discharge. The material of the first dielectric member 231 may be ceramic or silicon. The material of the second dielectric member 232 may be ceramic or silicon. The thickness of the conductive electrode 233 may be several micrometers to several hundreds of micrometers. The material of the conductive electrode 233 may be gold, silver, copper, or a molybdenum-manganese alloy. The conductive electrode 233 may be formed of a conductive material after being thermally processed in the second dielectric member 232. Preferably, the thickness of the conductive electrode 233 may be 10 to 15 micrometers. The conductive electrode 233 may be formed in a thin conductive pattern or in a thin plate shape.

The electrode case 215 is provided with a mounting portion 216 recessed from one surface thereof. An elastic body 219 is provided between the mounting portions 216 of the electrode unit 230. Thus, the electrode part 230 vibrates at the time of discharge, and radicals can be emitted to the surroundings. The elastic body 219 may be, for example, a coil-shaped spring, but may be a plate-like spring. Also, the electrode unit 230 itself may be made of a member having an elastic property.

FIG. 10 is the drawing of the electrode case 315 and electrode unit 330 according to Embodiment 3.

The electrode case 315 is detachably coupled to the rear case 113. For this, a guide protrusion is formed on the inner circumference of the electrode case 315, and a guide may be formed on the outer circumference of the rear case 113. Thus, the electrode case 315 is screwed or fitted to the rear case 113.

The electrode unit 330 according to the third embodiment is formed such that two wires are twisted to each other. The electrode unit 330 is detachably mounted to the mounting portion 316 recessed from one surface of the electrode case 315. The electrode unit 330 forms atmospheric plasma by the applied electric power. The electrode unit 330 may include a first conductive unit 331 and a second conductive unit 332 to generate a dielectric barrier discharge for atmospheric pressure plasma.

Electrodes 330 may include the first conductive unit 331 of wire shape extending in a first direction, and the second conductive portion 332 surrounding the first conductive unit 331 and having wire-shaped and twisted to form a plurality of turns.

At least one of the first conductive unit 331 and the second conductive unit 332 may include an insulating coating layer. The first conductive unit 331 and the second conductive unit 332 are closely disposed, and a dielectric barrier discharge may be generated between the first conductive unit 331 and the second conductive unit 332.

One of the conductive unit s may be connected to the alternating current generating member 170 and the other may be electrically connected to the ground.

Each of the first conductive unit 331 and the second conductive unit 332 may include an insulating coating. The first conductive unit 331 may include a conductive wire and an insulating sheath, and the second conductive portion 332 may include a conductive wire and an insulating sheath.

The insulating sheath may be 20 micrometers to 200 micrometers thick. The thickness of the insulating coating is preferably thin. However, if the thickness of the insulating coating is too thin, a dielectric breakdown may occur.

The diameter of the first conductive part 331 and the second conductive part 332 may be 0.5 mm to 2 mm. The thickness of the first conductive part 331 may be selected according to the degree of providing flexibility. When the first conductive portion 331 and the second conductive portion 332 are twisted together, the diameter of the first conductive portion 331 and the second conductive portion 332 may preferably be the same. The material of the conductive part may be copper, and the insulating coating may be enamel.

For the dielectric barrier discharge, one of the first conductive portion 331 or the second conductive portion 332 is coated with an insulating coating. Alternatively, both of the first conductive portion 331 and the second conductive portion 332 can be coated with an insulating coating. In this case, the dielectric constant is increased and a stable discharge of plasma can be induced.

The first conductive portion 331 is connected to the AC generating member 170 and the second conductive portion 332 is grounded. In the dielectric barrier discharge, the conductive units use twisted conductive wires that are in close contact with each other in order to keep the interval between the electrodes constant. Accordingly, the dielectric discharge electrode can be easily formed without a separate patterning step.

The first and second conductive parts 331 and 332 may be twisted to each other in a helical shape. The first conductive portion 331 may be applied to the positive voltage of the alternating current generating member 170 and the second conductive portion 332 may be applied to the negative voltage of the alternating current generating member 170. A high voltage alternating current pulse can be applied between the first conductive portion 331 and the second conductive portion 332. Accordingly, a dielectric barrier discharge can be generated between the first conductive portion 331 and the second conductive portion 332. The plasma generation region can be formed at a location that maintains an optimum discharge interval on the axis of symmetry of the conductive portion. The conductive portions that are twisted with each other can apply a high electric field, relative to the planar electrodes arranged on the same plane. Thus, the start voltage of discharge can be reduced. Further, since the conductive portion uses a flexible conductive wire, it can be deformed into various shapes, and can be manufactured easily and cost can be saved.

The electrode case 315 is formed with a mounting portion 316 recessed from one surface thereof. An elastic body 319 is provided between the electrode unit 330 and the mounting portion 316. As a result, the electrode unit 330 is vibrated at the time of discharge, and radicals can be emitted to the surroundings. The elastic body 319 may be, for example, a coil-shaped spring, but may be a plate-shaped spring. Also, the electrode unit 330 itself may be made of a member having elasticity.

In order to compare the performance of the conventional skin modifying agent according to the embodiment of the present invention with that of the conventional skin modifying agent, a skin whitening and wrinkle reducing performance were evaluated after conducting clinical experiments on experimental group A and experimental group B as shown in the following table.

TABLE 1

|  | Group A | Group B |
| --- | --- | --- |
| Whitening Effect | 22.69% improvement | 3.26% improvement |
| Wrinkle reducing effect | 44.24% improvement | 12.24% improvement |

The above Table 1 shows the experiment results that twenty women aged 35 and over were selected for each experiment for 6 weeks.

Experimental group A was massaged for 10 minutes by pushing outward from the inside of the face for 10 minutes using the beauty care device 100 according to the first embodiment, after cleansing every evening for 6 weeks during the test period. After that, 'Aloe Vera Soothing Gel' was evenly spread and absorbed. Experimental group B was soaked in an equal amount of the same Aloe Vera soothing gel in the same area as experimental group A, every evening after cleansing for 6 weeks.

During the experiment period, the use of functional cosmetics or beauty equipment, which may affect the results of the experiment other than the above-mentioned experiment products, was totally prohibited, and neither packs nor massages were applied.

The whitening effect was measured by using a spectrophotometer, and the average value was measured three times in succession at the same position and with the uniform illumination. Accordingly, the skin tones of 20 women were measured and the average value was calculated. The wrinkle reducing effect was measured using "PRI MOS Lite", using the result of 3D matching after three consecutive shots of the right eye wrinkle using the test equipment, and finally calculating the average value after the skin tones of 20 women were measured.

As shown in Table 1, it was confirmed that the skin whitening effect and the wrinkle reducing effect were improved by using the beauty care device 100 according to the embodiment of the present invention which increases skin penetration effect of skin improving agent as compared with that using only the conventional skin-improving agent for supplying nutrition and moisture to the skin.

The above-described plasma-based beauty care device is not limited in the configurations and methods of the above-described embodiments. Various modifications can be made by using the above embodiments by selectively combining all or a part of such embodiments.

The device for use in beauty care according to the disclosed embodiments of the present invention can be used for the manufacture of various beauty care devices for reducing wrinkles, improving the skin elasticity, and enhancing other beneficial effects.

What is claimed is:

1. A skin treatment device by application of plasma to a skin, the device comprising:
   a body having a handle; and
   an electrode unit generating an atmospheric pressure plasma by application of electric power,
   wherein first and second grounds are provided on two opposite sides of the handle, respectively,
   wherein the electrode unit is detachably attached to a mounting portion recessed from one surface of the body,
   wherein the electrode unit comprises:
      a first film, a second film, and a third film laminated together; and
      a first conductor disposed between the first and second films, and a second conductor disposed between the second and third films, such that a dielectric barrier discharge is generated between the first and the second conductors
   wherein the body further comprises at least two springs disposed between the electrode unit and the mounting portion of the electrode unit to facilitate vibrating the electrode unit, and is configured to emit radicals to the surroundings at the time of discharge by vibrating the electrode unit.

2. A skin treatment device by application of plasma to a skin, the device comprising:
   a body having a handle; and
   an electrode unit generating an atmospheric pressure plasma by application of electric power,
   wherein first and second grounds are provided on two opposite sides of the handle, respectively,
   wherein the electrode unit is detachably attached to a mounting portion recessed from one surface of the body,
   wherein the electrode unit comprises:
   a first dielectric member having a plate shape, a second dielectric member laminated on the first dielectric member, and a conductive electrode disposed between the first and second dielectric members, such that a dielectric barrier discharge is generated between the first and second dielectric members and the conductive electrode,
   wherein the body further comprises at least two springs disposed between the electrode unit and the mounting portion of the electrode unit to facilitate vibrating the electrode unit, and is configured to emit radicals to the surroundings at the time of discharge by vibrating the electrode unit.

3. A skin treatment device by application of plasma to a skin, the device comprising:
   a body having a handle; and
   an electrode unit generating an atmospheric pressure plasma by application of electric power,
   wherein first and second grounds are provided on two opposite sides of the handle, respectively, wherein the electrode unit is detachably attached to a mounting portion recessed from one surface of the body, wherein the electrode unit comprises:

a first conductive unit in the form of a wire;

a second conductive unit surrounding the first conductive unit and twisted to form a plurality of turns; and an insulating sheath formed on at least one of the first and second conductive units so as to generate a dielectric barrier discharge, wherein the body further comprises at least two springs disposed between the electrode unit and the mounting portion of the electrode unit to facilitate vibrating the electrode unit, and is configured to emit radicals to the surroundings at the time of discharge by vibrating the electrode unit.

4. The skin treatment device according to claim 1, wherein the body further comprising an AC generator for supplying power to the conductors.

5. The skin treatment device according to claim 4, wherein one of the conductors is electrically connected to one of the grounds.

6. The skin treatment device according to claim 4, wherein the electrode unit is configured to have a wide band shape elongated in the longitudinal direction to generate plasma at a larger area, wherein both sides of the electrode unit are detachably coupled to the body.

7. The skin treatment device according to claim 1, wherein the first conductor and the second conductor are spaced apart from each other so as not to be laminated when projected on one surface thereof, wherein at least one of the first and second conductors include at least three or more conductive lines that are divided in branches.

* * * * *